(12) United States Patent
Dimino et al.

(10) Patent No.: US 10,925,617 B2
(45) Date of Patent: Feb. 23, 2021

(54) INTUITIVELY AND RAPIDLY APPLICABLE TOURNIQUETS

(71) Applicants: Michael J. Dimino, Freehold, NJ (US);
Michael C. Dimino, Freehold, NJ (US);
Alfonse Dimino, Freehold, NJ (US)

(72) Inventors: Michael J. Dimino, Freehold, NJ (US);
Michael C. Dimino, Freehold, NJ (US);
Alfonse Dimino, Freehold, NJ (US)

( * ) Notice: Subject to any disclaimer, the term of this patent is extended or adjusted under 35 U.S.C. 154(b) by 249 days.

(21) Appl. No.: 15/833,626

(22) Filed: Dec. 6, 2017

(65) Prior Publication Data
US 2018/0153557 A1 Jun. 7, 2018

Related U.S. Application Data

(63) Continuation-in-part of application No. 29/579,266, filed on Sep. 29, 2016, now Pat. No. Des. 825,752,
(Continued)

(51) Int. Cl.
*A61B 17/132* (2006.01)
*A61B 5/03* (2006.01)
(Continued)

(52) U.S. Cl.
CPC ............ *A61B 17/1327* (2013.01); *A61B 5/03* (2013.01); *A61B 17/1325* (2013.01); *A61B 5/01* (2013.01);
(Continued)

(58) Field of Classification Search
CPC .............. A61B 17/132; A61B 17/1322; A61B 17/1325; A61B 17/1327; A61B 17/135; Y10T 24/1424; Y10T 24/14
See application file for complete search history.

(56) References Cited

U.S. PATENT DOCUMENTS 5,193,254 A * 3/1993 Geisinger ............... E05B 75/00
24/16 PB
5,269,803 A * 12/1993 Geary ................ A61B 17/1322
606/201

(Continued)

FOREIGN PATENT DOCUMENTS

WO    WO2016/172599    * 10/2016

*Primary Examiner* — Thomas McEvoy
(74) *Attorney, Agent, or Firm* — Ostrolenk Faber LLP

(57) ABSTRACT

A tourniquet includes a strap formed of a flexible material and shaped as a long, thin and generally flat body having a first surface and an opposed second surface, and an array of ridges extending transversely, substantially along most of the first surface. The tourniquet head includes an insertion mouth and within the mouth a flexible support and a plurality of teeth formed on the flexible support. The flexible support and the plurality of teeth providing an insertion channel in the tourniquet head for tightly receiving a free insertion end of the strap in a manner that enables the strap to be threaded through the insertion mouth with the plurality of teeth in the head being lockable on the ridges on the strap in a manner that enables a leading end of said strap to be ratcheted through the mouth in a locking direction only. A release lever enables the flexible support in the mouth to be pulled away from the ridges on the strap to allow for temporary disengaging of the teeth in the head from the ridges on the strap, to enable gradual and controlled releasing of tourniquet tension being applied on a body part to which the tourniquet has been mounted.

32 Claims, 19 Drawing Sheets

Related U.S. Application Data and a continuation-in-part of application No. 29/607,446, filed on Jun. 13, 2017.

(51) Int. Cl.
| | |
|---|---|
| *A61B 5/145* | (2006.01) |
| *A61B 17/00* | (2006.01) |
| *A61B 90/00* | (2016.01) |
| *A61B 5/0205* | (2006.01) |
| *A61B 5/024* | (2006.01) |
| *A61B 5/01* | (2006.01) |
| *A61B 5/11* | (2006.01) |
| *A61B 5/00* | (2006.01) |

(52) U.S. Cl.
CPC ........... *A61B 5/024* (2013.01); *A61B 5/02055* (2013.01); *A61B 5/1112* (2013.01); *A61B 5/14521* (2013.01); *A61B 5/14532* (2013.01); *A61B 5/14542* (2013.01); *A61B 5/7405* (2013.01); *A61B 2017/00084* (2013.01); *A61B 2017/00115* (2013.01); *A61B 2017/00407* (2013.01); *A61B 2017/00853* (2013.01); *A61B 2017/00862* (2013.01); *A61B 2017/00955* (2013.01); *A61B 2090/034* (2016.02); *A61B 2090/064* (2016.02); *A61B 2090/0807* (2016.02); *A61B 2562/0247* (2013.01)

(56) References Cited

U.S. PATENT DOCUMENTS

| | | | |
|---|---|---|---|
| 6,217,601 B1 * | 4/2001 | Chao | A61B 17/1325 606/203 |
| 8,652,164 B1 * | 2/2014 | Aston | A61B 17/1327 606/203 |
| 2010/0115738 A1 * | 5/2010 | Kuhne | B65D 63/1063 24/271 |

* cited by examiner

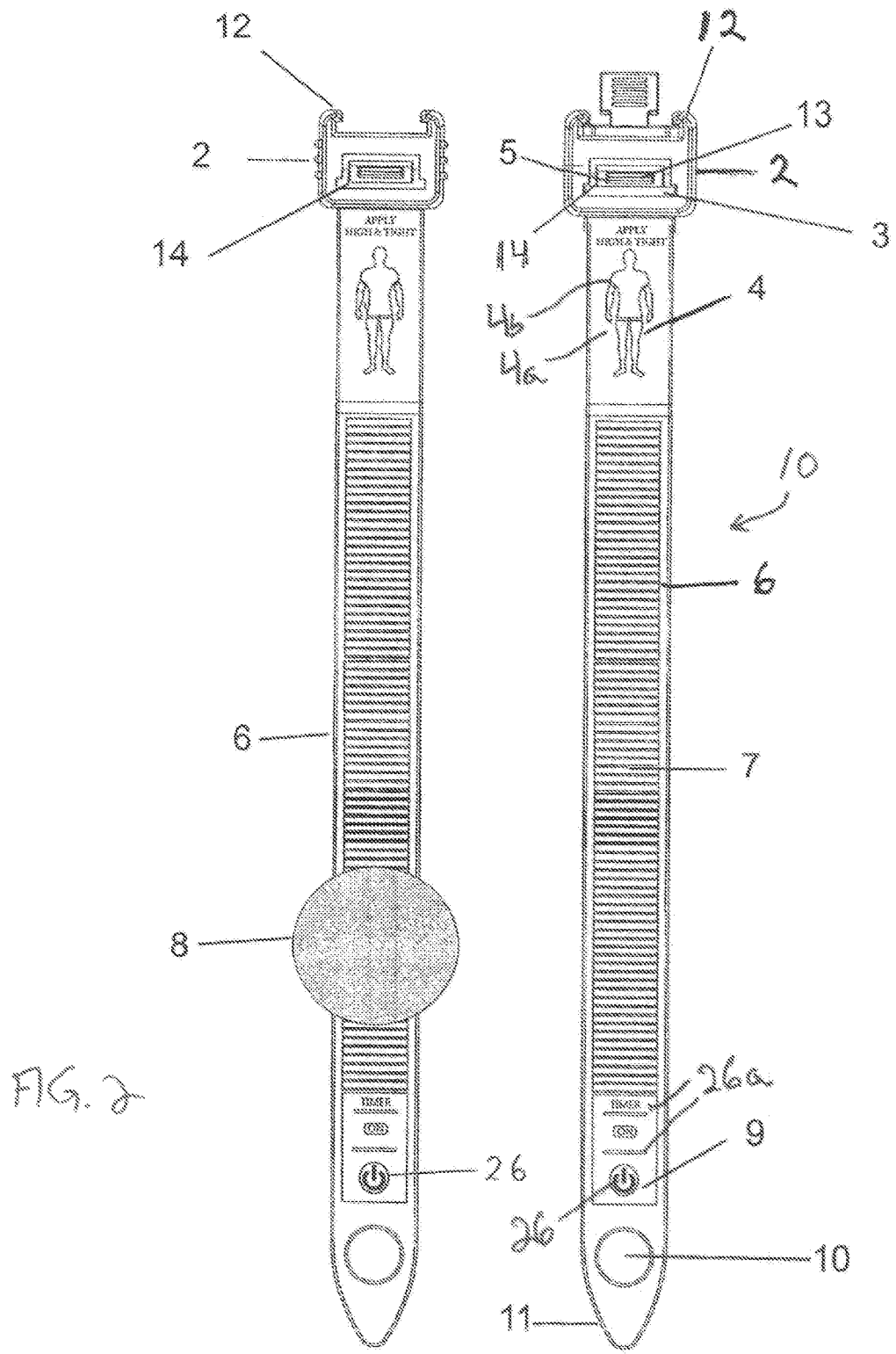

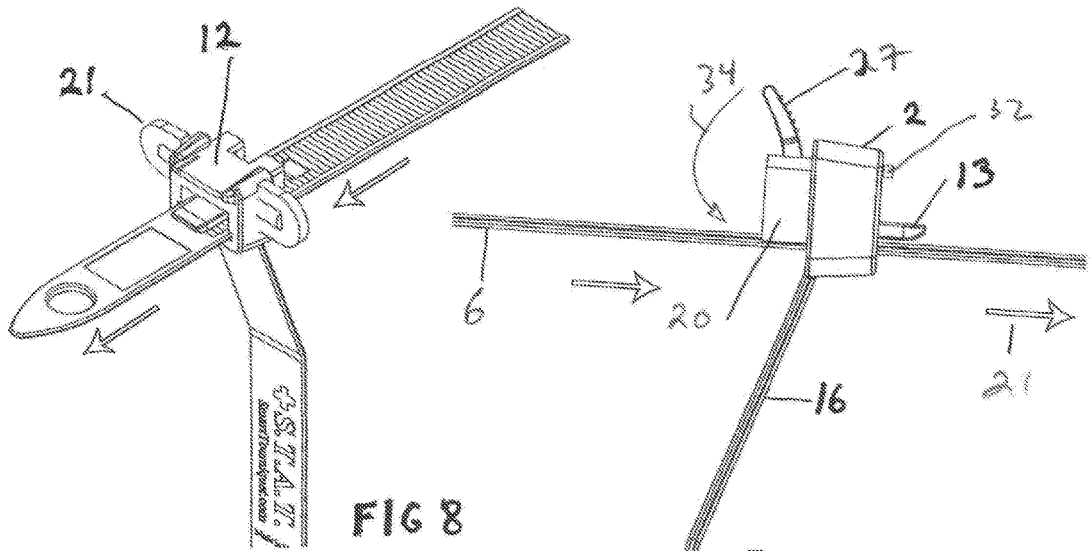
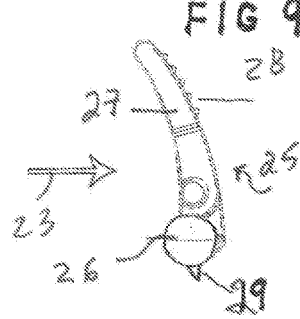
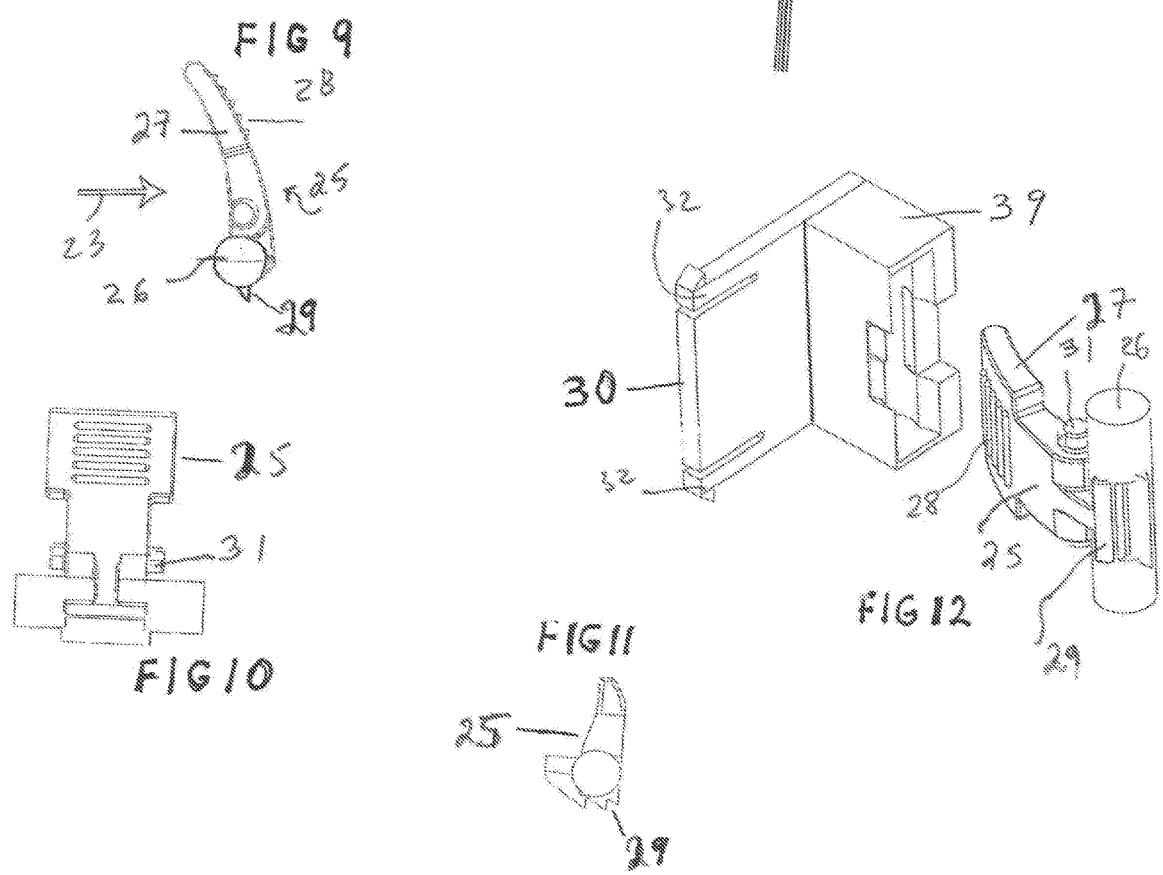
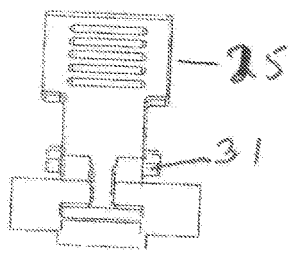
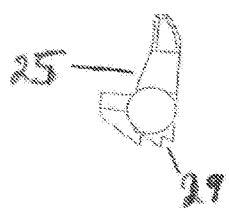

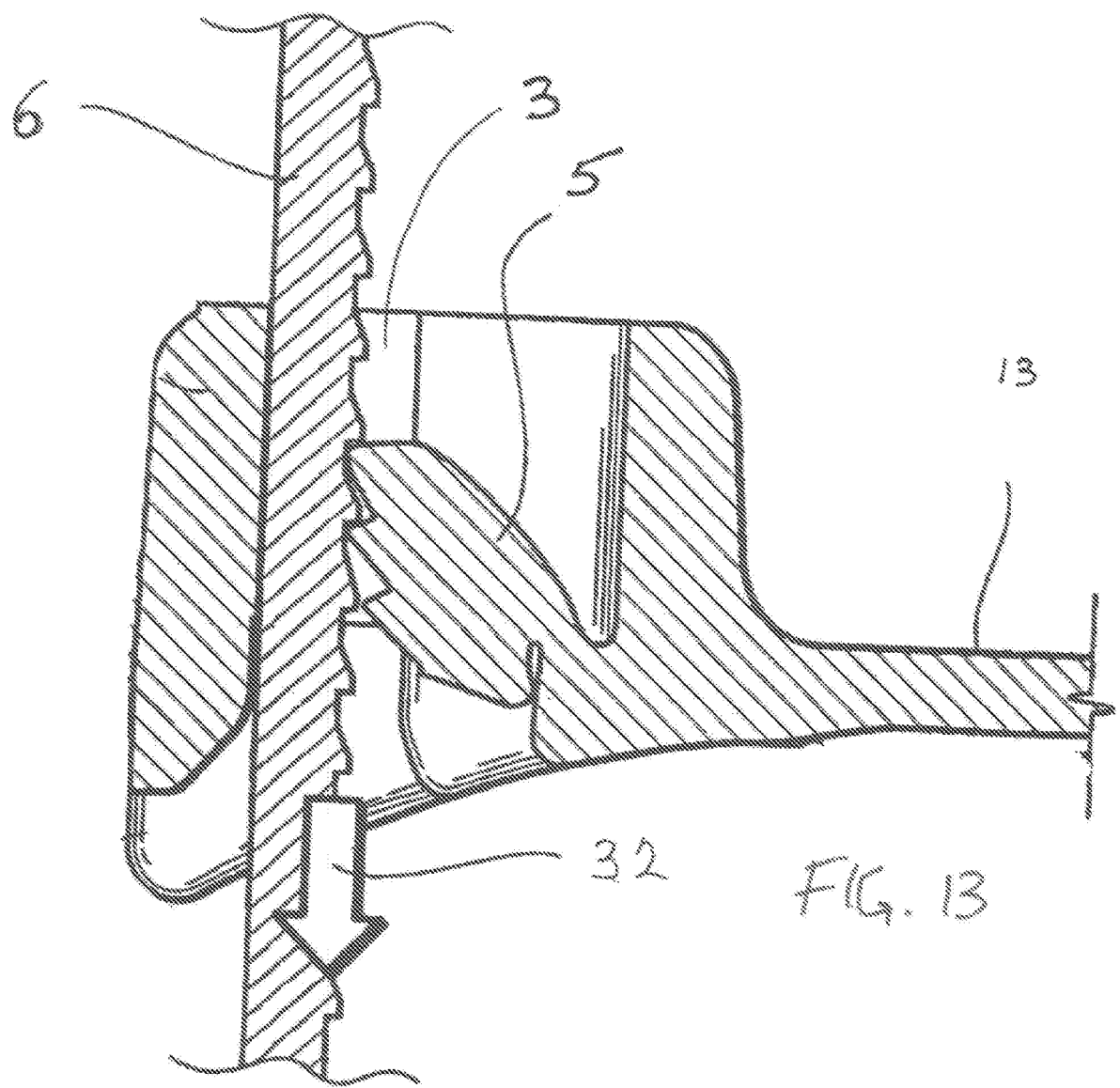

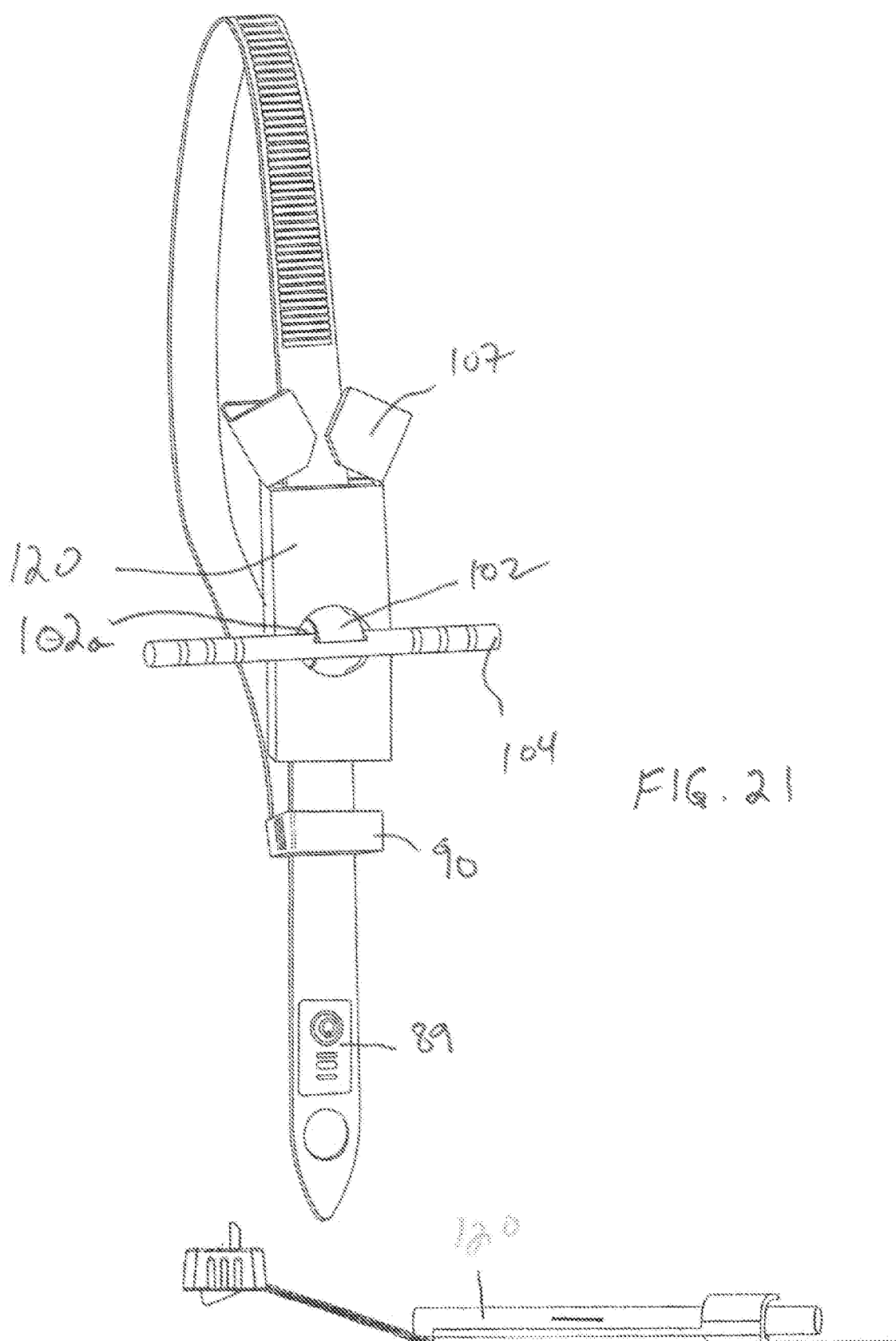

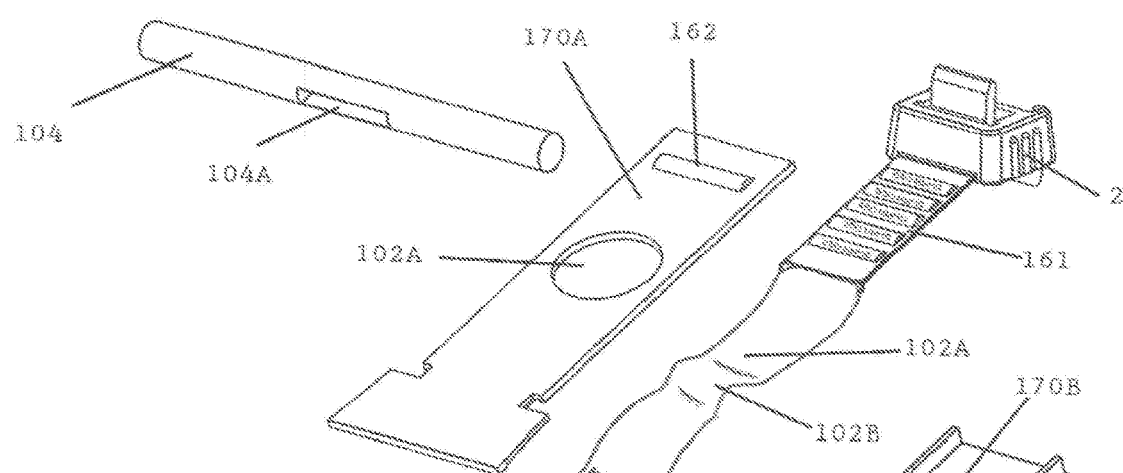
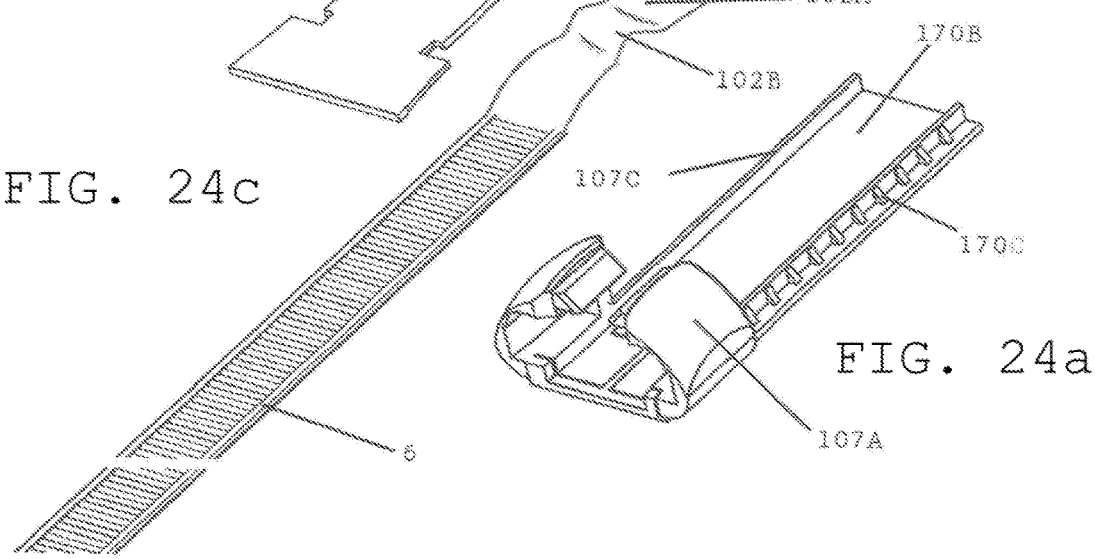

INTUITIVELY AND RAPIDLY APPLICABLE TOURNIQUETS

CROSS-REFERENCE TO RELATED APPLICATIONS

This application claims benefit under 35 U.S.C. § 119(e) to Provisional Application Ser. No. 62/509,614, filed on May 22, 2017, the disclosure of which is incorporated herein by reference in its entirety. This application is also a Continuation-in-Part of application Ser. No. 29/579,266, filed Sep. 29, 2016 and application Ser. No. 29/607,446, filed Jun. 13, 2017.

BACKGROUND OF THE INVENTION

The present invention relates generally to tourniquets and, more particularly, to tourniquets that are intuitively and rapidly applicable to human limbs and organs to quickly arrest bloods flows. These tourniquets can be very reliably donned on a person needing immediate arresting of blood flow, in a matter of only a few seconds rather than several minutes.

As is well known, tourniquets are devices that are designed to be applied to a limb for the purposes of constricting blood flow to that limb by applying pressure in order to limit the effects of extreme blood loss.

Tourniquets are typically used in the temporary treatment of extremity injuries, high damage to the body, arms and/or legs, which result in gushing blood, a condition that can become critical and life threatening very rapidly. The situation can become particularly critical in battlefield scenarios where the injuries can be very severe and the locations of field or permanent hospitals are at some distance away. This requires critical knowledge and ability in applying tourniquets to maintain the patient in a condition that the injury can be dealt with at the hospital after some time has lapsed.

The need to provide omnipresent and widespread abilities to apply tourniquets to serious wounds has intensified in this age, in the post-9/11 world, where violent threats and terrorist attacks are every day and everywhere occurrences as exemplified by school mass shootings, bombings, vehicle attacks and the like that are the subject of constant reporting in the press. These attacks cause trauma wounds and hemorrhaging to the extremities and in some cases loss of limb if not immediately treated. The victim is at the risk of dying from blood loss within 90 seconds to five minutes.

Indeed, the United States White House and Homeland Security Offices have begun a campaign called "Stop the Bleed." It calls for worldwide distribution of tourniquets to be placed in schools, vehicles, first responder facilities, office buildings, airports, stadiums, outdoor events, at law enforcement facilities and everywhere it is common to provide first aid kits, defibrillators and the like.

The current tourniquets in use nowadays require prior training in order to apply properly. The current application time is at least five minutes. A tourniquet is urgently needed that anyone would be able to apply within a few seconds, even by a bystander without any prior training because no matter how fast a first responder may arrive, the bystander will always be first on the scene. The present inventors believe that the tourniquet embodiments described herein can be applied within seconds because they employ familiar zip-tie technology that allows almost anyone to quickly comprehend its mechanism and mode of use, to apply the tourniquet to the person(s) needing the treatment within seconds.

A considerable body of prior art has developed in relation to the devices that are the subject of the present invention. This prior art is exemplified by U.S. Pat. No. 6,746,470 that describes a pneumatic tourniquet adapted for self-application. U.S. Patent Application Publication No. 2010/0234877 describes a tourniquet with a display of duration of use. U.S. Patent Application Publication No. 2008/0177159 similarly describes a timer for tourniquets. U.S. Patent Application Publication No. 2010/0160957 describes a one-handed loop tourniquet with a lockable feature. U.S. Pat. No. 8,926,651 describes a self-locking tourniquet and an automated timer. The contents of the aforementioned U.S. patents and patent applications are incorporated by reference herein.

The prior art is further exemplified by the tourniquet tightening mechanism that is described in U.S. Pat. No. 7,842,067, by the disclosure in U.S. Pat. No. 7,096,543 and by U.S. Patent Publications 2011/0137336 and 2010/0234877, the entire contents of which patents and patent applications are incorporated by reference herein.

Still, the prior art has fallen short in providing a single solution, tourniquet device that is so constructed that its use is rendered intuitive to even non-medical lay persons, and which can be quickly applied to a limb or organ, e.g. around the stomach of an injured person, in a manner that will stabilize the life threatening injury suffered by the injured person at an airport, train station and the like where many persons may be injured at once and where fellow travelers can assist in applying these devices to the injuries by obtaining these devices from handy nearby dispensers where they are stored to be used in emergency situations.

SUMMARY OF THE INVENTION

It is an object of the present invention to provide tourniquets that effectively and quickly occludes the flow of blood from limbs and the like, with sufficient pressure being applied to largely or even completely halt the life threatening blood flow.

It is a further object of the present invention to provide tourniquets of the above type that incorporate features that make them intuitive to apply to limbs and the like, even by lay persons.

It is yet a further object of the invention to provide tourniquets of the above type that are mechanically simply and comparatively inexpensive so as to make them practical to be stored everywhere in public gathering places, where large scale attacks may be perpetrated, in military settings and the like.

The foregoing and other features of the invention are realized by tourniquets that, in accordance with preferred embodiments thereof, include a tourniquet, comprising: a strap formed of a flexible material and being shaped as a long, thin and generally flat body having a first surface and an opposed second surface, and an array of ridges extending transversely, substantially along most of the first surface; a tourniquet head including an insertion mouth and within the mouth there being provided a flexible support and a plurality of teeth formed on the flexible support, said flexible support and said plurality of teeth providing an insertion channel in the tourniquet head for tightly receiving a free insertion end of the strap in a manner that enables the strap to be threaded through the insertion mouth with the plurality of teeth in the head being lockable on the ridges on the strap in a manner that enables a leading end of said strap to be ratcheted through the mouth in a locking direction only; and a release lever that enables said flexible support in the mouth to be pulled away from the ridges on the strap to allow for temporary disengaging of the teeth in the head from the ridges on the strap, to enable gradual and controlled releasing of tourniquet tension being applied on a body part to which the tourniquet has been mounted.

In accordance with preferred embodiments, the tourniquet further includes at least one holding device configured to be coupled to the strap, at a desired location on the strap, said holding device being configured to be optionally placed on an injury location on the human body part, the holding device holding one or more of; a pressure sensing device, medicinal material, a temperature sensor, a light emitter, a sound emitter, a GPS location sensor, a pulse sensor, an oxygen level blood saturation sensor, a gauze coated with blood coagulant, a perspiration sensor and an LCD screen. The is configured to increase the pressure on the human body part by holding the head thereof in one hand and pulling on a tail end of a strap with another hand and further including a separate ratcheting lever that is configured to enable further tightening of the strap, to increase the tension exerted by the tourniquet by ratcheting the ratcheting lever to engage the ridges on the strap, one ridge at a time. The head comprises a dangling strap holding clip for holding a dangling portion of the strap down over the release lever on head, to prevent undesired releasing of tourniquet pressure being applied to the human body part. The strap may include an angled portion that extends from the head for at least several inches of the strap, which is configured to prevent pinching of a user's skin. The head may have a separate lever located at the back wall of the head that allows for pressure against the release lever that presses the release lever forward to allow more pressure when the release lever interlocks with the teeth on the strap.

In accordance with preferred embodiments, the head of the tourniquet is configured to allow insertion there-into of another tourniquet strap to provide a combined length strap, having close to double a length of said tourniquet, allowing binding of extremities together and/or supporting a fractured hip or a fractured skull. The GPS location sensor comprises a cellular satellite transceiver module that transmits GPS coordinates of the tourniquet to a remote location, the transceiver module provides for two-way voice communication. The strap has, adjacent its insertion end, a pulling opening through which a finger can be inserted to tightly grasp the strap when being pulled, without slipping.

In accordance with preferred embodiments, the tourniquets include a timer that is initiated at the time when the tourniquet is applied around the human body part. The timer comprises several strips adhered to one another and including a channel in the strips, a number of reservoir windows which indicate the amount of time that has elapsed since the tourniquet has been applied. The timer is removably attachable to the strap adjacent its insertion end, so it is capable of being activated either manually or automatically when the strap is inserted into the insertion mouth of the head. The timer may be comprised as a digital timer. Visually perceptible instructions for mounting the tourniquet around the human body part may be included. The visual indication comprises the silhouette of a human body illustrating locations where the tourniquet should be applied.

In accordance with preferred embodiments, the holding device may hold a medical patch that includes a medicinal chemical that fuses into the human body part which it contacts. The device holder is configured to hold a location indicator that emits one of visible light and infrared radiation, to allow visible location of a victim bearing the tourniquet. The temperature sensor comprises a temperature sensor that reads body temperature.

In accordance with preferred embodiments, the tourniquet is provided in a package with its insertion end already threaded through the insertion mouth at the head, so it is ready to be deployed during emergencies without loss of time by simply being placed around a human limb and then tightened.

In accordance with preferred embodiments, the tourniquet comprises an auxiliary tourniquet tensioning device with a tensioning rod that can be twisted to shorten the length of the strap to increase a tension being applied to the human body part, which may be formed as a windlass tension mechanism. The windlass tension mechanism comprises a flexible plastic base plate interposed between the head and the strap, and the plastic plate which is joined together by a fabric material. The fabric material passes through the tensioning rod, so that when the tensioning rod is twisted, the fabric material shortens in circumferential dimension of the tourniquet on the human body part. A clip mechanism prevents the tensioning rod from untwisting. The plastic locking head and ridged strap eliminates the problem of tourniquet failure (loosening of the tourniquet strap when victim moves is a problem that has been experienced by windlass tourniquets using tourniquets that use Velcro straps).

In accordance with preferred embodiments, the ridges on the strap are spaced at a pitch in the range of 1 to 3 mm, to allow very fine adjustment of the tension being applied to the human body part. The strap may be formed of a material that is bullet, oil, water and dirt resistant, and self-sealing. Pulling the insertion end of the strap through the head produces audible sounds as each ridge on the strap passes over the teeth in head to provide an audible indication of a properly working tourniquet. The plastic material of said strap is capable of withstanding temperatures of −55° to 155° Fahrenheit, without losing its functionality. The pressure indicating device that senses the pressure that is applied by the strap of the tourniquet to the human body part may indicate pressure in units of pressure which is indicated in one or more of a pressure a force reading provided either in pounds or millimeters of mercury (mmHg). Each number can be color coded for easy visual reading.

In accordance with preferred embodiments, the tourniquet comprises: a strap portion and a buckle shaped head portion, wherein the strap portion comprises an elongated and flexible strip with an insertion end and a opposed end that is physically attached to the head portion of the tourniquet, said head portion comprising an insertion mouth through which said insertion end of the strap is inserted and pulled therethrough, the head including a locking pin and the strap comprising a series of locking holes into which the locking pin is inserted to maintain the tension of the tourniquet around a human body part and further including a timer that is manually activated by pushing down on a reservoir of the timer which releases liquid that begins to flow into indicator windows and is capable of indicating one of at least two elapsed time periods.

Other features and advantages of the present invention will become apparent from the following description of the invention which refers to the accompanying drawings.

BRIEF DESCRIPTION OF THE DRAWINGS

FIG. 1 diagrammatically depicts a tourniquet of the present invention, according to a first embodiment thereof.

FIG. 2 diagrammatically depicts the tourniquet embodiment of FIG. 1 with a pressure point device included.

FIGS. 7-12 show a modified head with a further tension adjuster, that uses a ratcheting mechanism.

FIG. 13 shows a further modified locking head.

FIGS. 21 and 22 illustrate a cover feature for the tensioning rod of FIG. 16.

FIGS. 24a, 24b, 24c and 24d are an exploded view of the windlass device of FIG. 24.

DETAILED DESCRIPTION OF EMBODIMENTS OF THE INVENTION

Figure 3:
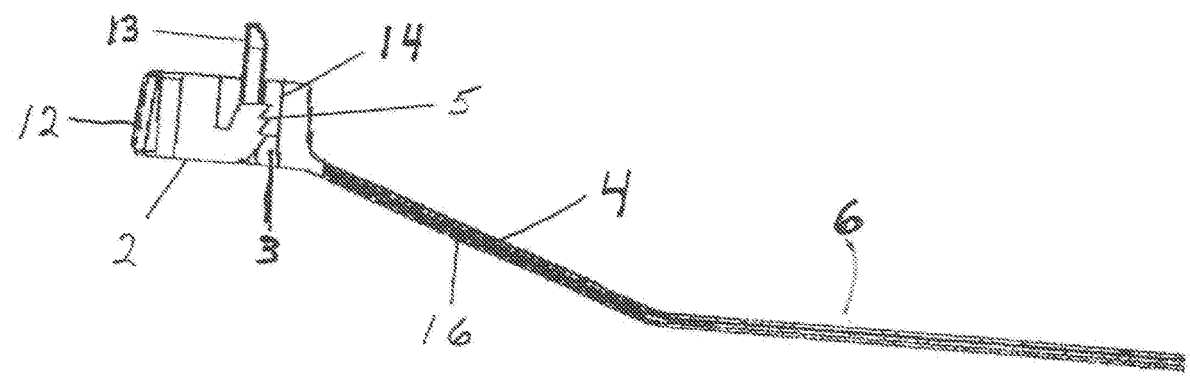
FIG. 3 is a cross-section through a head portion of the tourniquet of FIG. 1 to illustrate features thereof.

Referring to the drawings, initial reference is made to FIG. 1 which illustrates a tourniquet 10 of the present invention in accordance with one embodiment thereof in which the tourniquet comprises an elongated, narrow and thin, 1-3 mm thick plasticized strap body 6 with an insertable narrowed distal end/tail 11 which is insertable into a head 2 of the tourniquet 10 via an insertion opening 3. The insertion opening 3 is provided within with teeth 5 that engage complementary ridges 7 on the tourniquet strap 6, in a manner similar to tightening devices such as cable ties and the like. Pulling at the hole tab at the distal end 11, including by inserting a finger through the pulling opening 10, engages the teeth 5 and permits only further tightening, without allowing any loosening, except as noted below. That is, the body on the body on which the teeth 5 are provided can be coupled to a lever tension adjuster 13 which can be pivoted or pulled against the built-in resilience force of the adjuster 13 to temporarily disengage the teeth 5 from the ridges 7, to reduce the tension on the limb.

Figure 4:
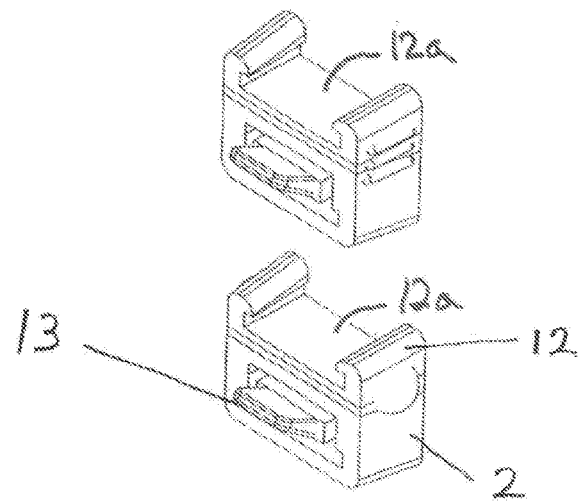
FIG. 4 is a perspective of the header portion of the tourniquet of FIG. 1.

The tourniquet strap body 6 of the present invention is conveniently provided at a location adjacent the distal end 11, with a timer 9 that contains a fluid reservoir 26, which when pressed releases a fluid pre-stored within the reservoir 26, thereby activating timer indicators 26a which changes their appearance, for example at the one half hour mark and at the one hour mark after the activation of the timer 9. Typically, when the distal end 11 is passed through the head, the narrowness of the opening will depress and burst the reservoir 26 causing the fluid to begin flowing out and the timer to be started. At the opposed end of the strap body 6, adjacent the head 2, a human FIG. 4 is depicted which shows the locations on the legs and arms 4a and 4b where the tourniquet 10 should be applied to the injured person.

Figure 18:
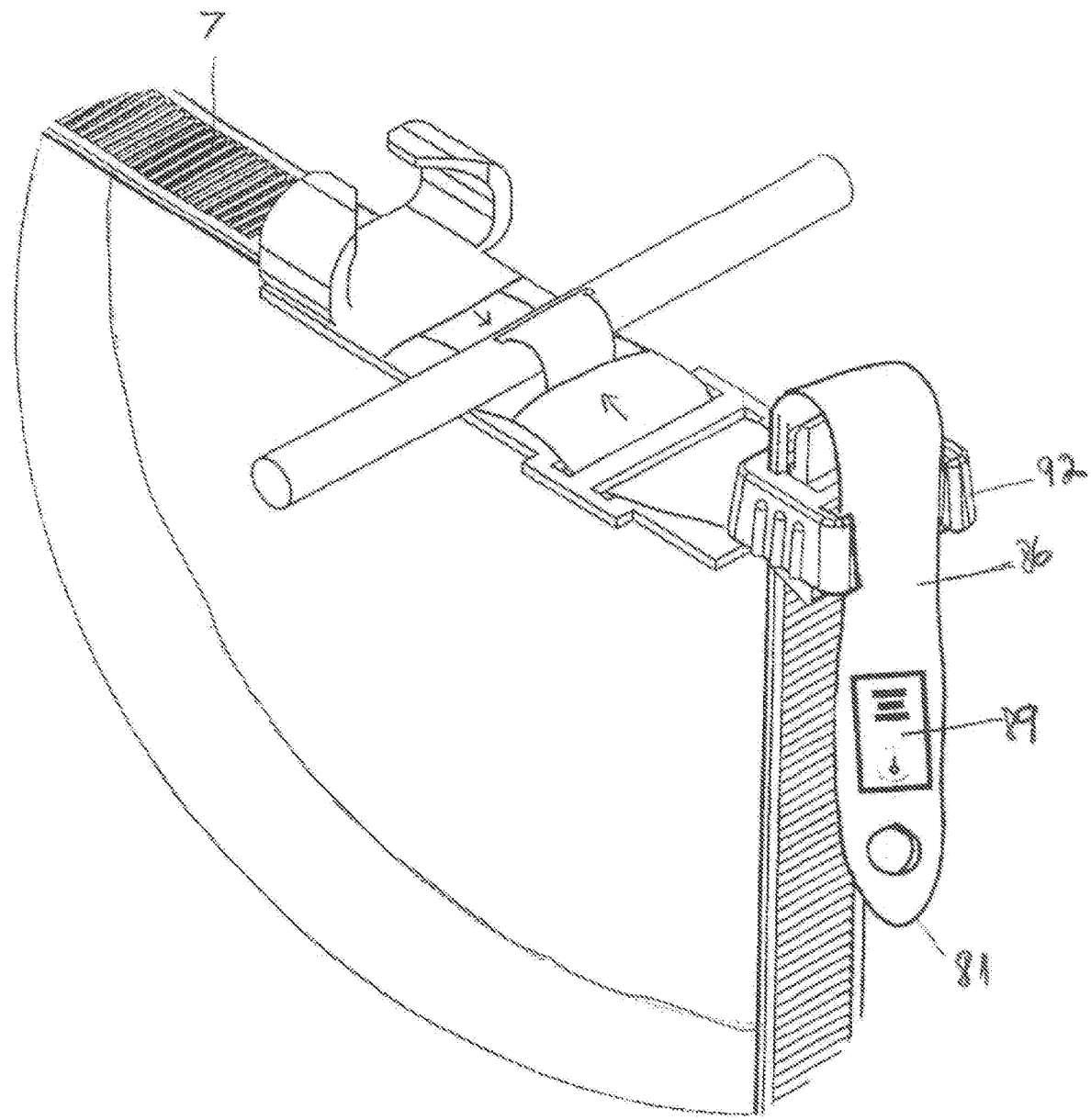

Once the tourniquet 10 has been sufficiently tightened, the excess strap protruding from the insertion mouth 3 can be threaded between the bent over sides 12 of the body of the head 2, in a space that has approximately the thickness of the strap body 6, as illustrated in FIG. 18. This feature serves as a safety mechanism, by covering the tension release lever 13 so that it is not accidentally activated to release the tourniquet tension.

Referring to FIG. 2, the strap body 6 can be provided with an enlarged, protruding and adjustably locatable pressure point device 8 that is designed to be positioned directly over a wound or an artery. For example, it has been determined that the pressure point device 8 can be placed over the open wound in a stomach to stop bleeding or to apply additional pressure on the wound or to hold pressure bandages or other devices against the wound. FIG. 2 also illustrates an embodiment which is generally similar to the embodiment of FIG. 1 but which is provided without a thumb lever tension adjuster 17 of the embodiment of FIG. 1.

The cross-sectional view of FIG. 3 illustrates the strap body 6 including a somewhat more rigid section 16 that is inclined at an angle of about 30 degrees relative to the major plane of the head 2, also illustrating the tension release lever 13 which is operatively coupled to the teeth 5 leaving a very narrow space 3 which defines the mouth 3 of the tourniquet 10.

Referring to FIG. 4, these perspective views of the head 2 of the tourniquet 10 show the tension release lever 13 and the overhang sections 12 that extend at a distance of a millimeter or so above the surface 12a, leaving left and right channels for holding the side edges of the strap body 6. When the strap body 6 excess or overhang is threaded under the overhangs 12, it serves as a safety cover for the tension release lever 13 and as a means that avoids any portion of the tourniquet from dangling or from being pulled in an unwanted manner. It also acts as a safety release lever cover for 13.

Figure 5:
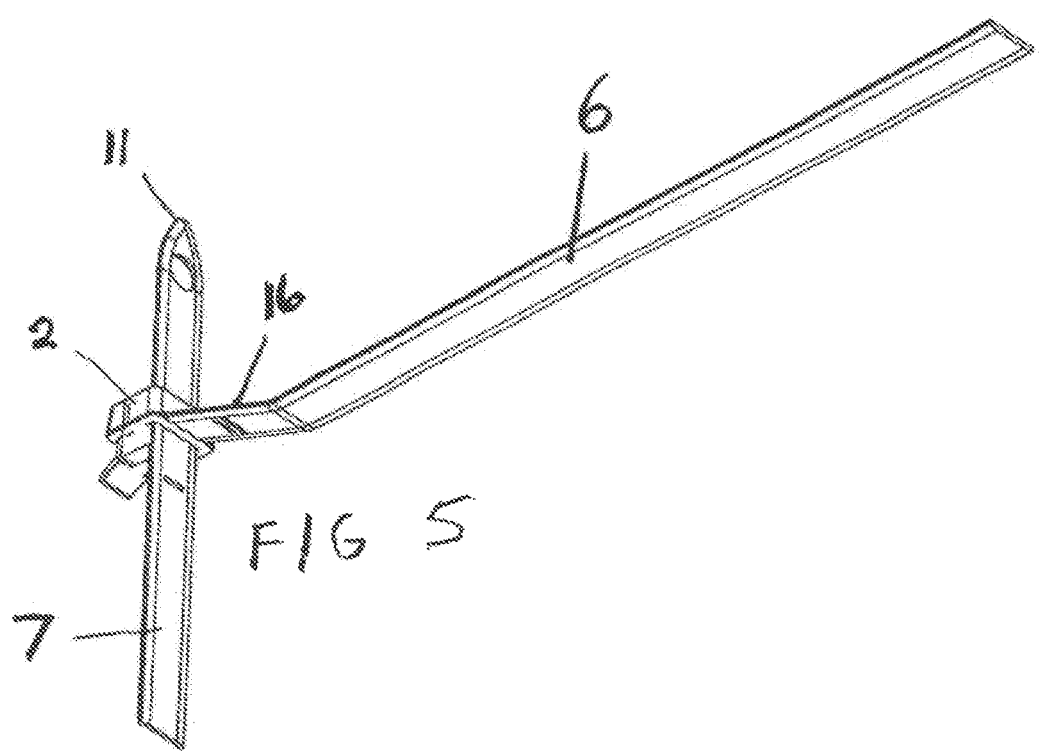
FIGS. 5 and 6 are perspectives showing the manner of use of the tourniquet of FIG. 1.
Figure 6:
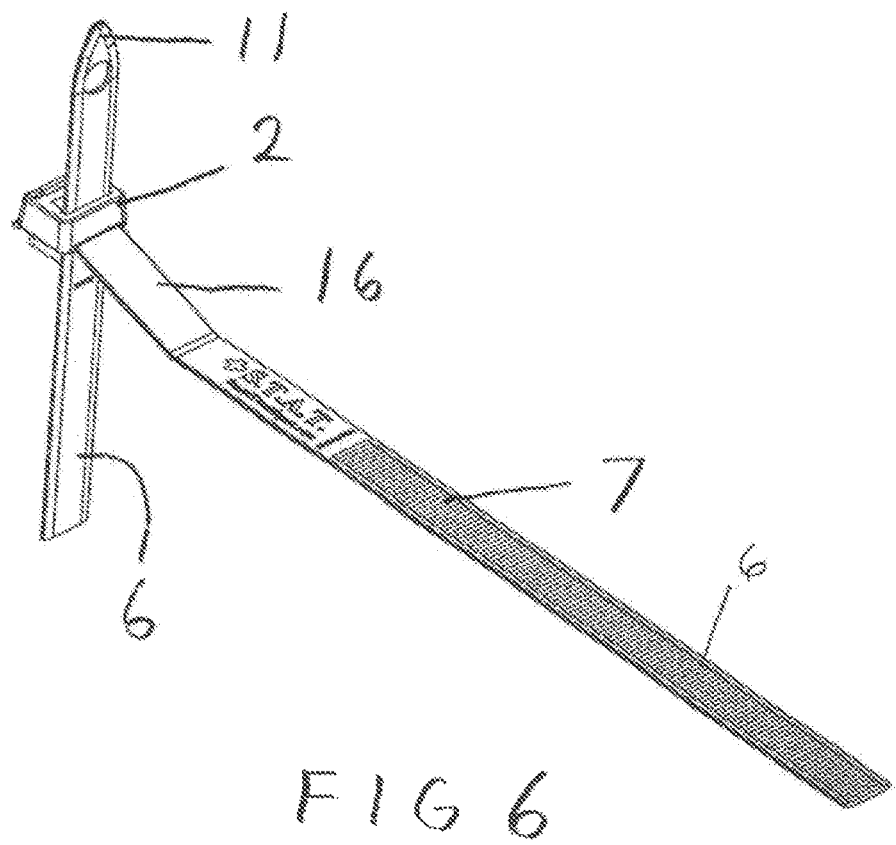

FIG. 5 perspectively illustrates the inside surfaces of the strap body 6, as well as the tail 11 which is inserted through the head 2. FIG. 6 illustrates the opposite side of the strap body that shows the ridges/teeth 7. Two or more tourniquets can be joined to form one larger tourniquet that then can be used on the torso or other body parts of a patient.

FIG. 8 is a perspective showing the direction of insertion of the strap through the head 2 and also shows the inclusion of ears 21 which help in grasping the head 2, while pulling on the strap 6 to tighten and increase the pressure being applied to the human body part, e.g. limb, stomach, head and the like.

FIG. 7 shows an auxiliary tensioning device 20 which utilizes a ratcheting mechanism to optionally increase the tension being applied by the tourniquet, after the initial tightening provided by the pulling of the strap through the head 2. The ratcheting device 20 comprises, as shown in FIG. 12, a block 30 and a ratchet lever 25 which are inter-assembled as shown in FIG. 7. The block 30 has catches 32 that pass through and lock inside the head 2. See FIG. 2.

The ratchet lever 25 includes an arm 27, knurled on side 28, which is coupled by pin 31 to the shaft 26 that is provided with ratcheting burrs 29. Thereby, when the ratchet arm 27 is pulled in the direction of the arrow 23 (FIG. 9), its burrs 29 engage the ridges 7 on the strap 6, and move the strap in the direction of the arrow 21 in a tightening direction. With each ratchet activation, the strap is tightened by the pitch of the ridges 7. This arrangement, whereby the length of the arm 27 is much greater that the mentioned pitch (about one millimeter or so), produces a great mechanical advantage that enables obtaining large tensions being applied to the body part requiring occlusion, even by a person who is weak or whose hands are trembling, etc.

FIGS. 10 and 11 show further details of this auxiliary tensioning mechanism 20.

In FIG. 13, a modified head has the teeth 5 connected to the body via a living hinge 5a that tends to turn the teeth holding body counter-clockwise, allowing the strap body 6 to be pulled upward to tighten but not allowing any give whatsoever in the direction of the arrow 32 to release the pressure on the limb.

Figure 14B:
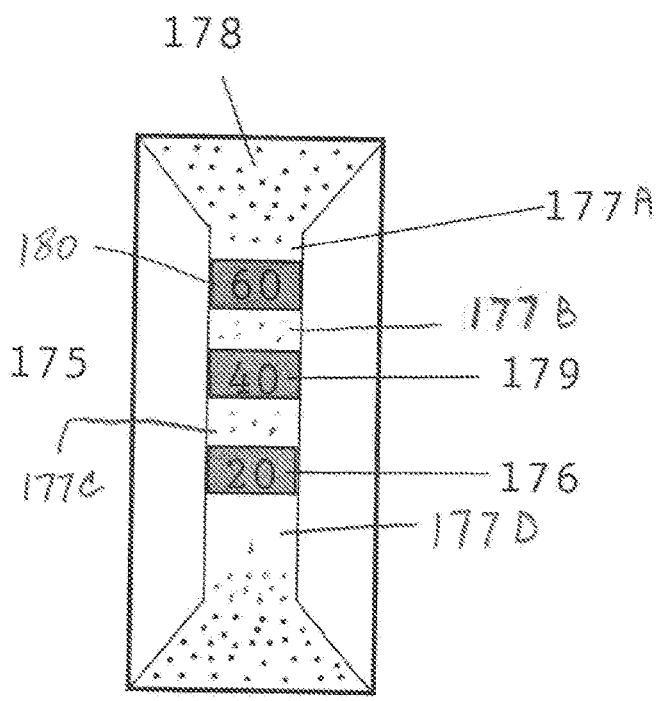
FIG. 14a and FIG. 14b explicate a timer component of the tourniquet of the present invention.
Figure 14A:
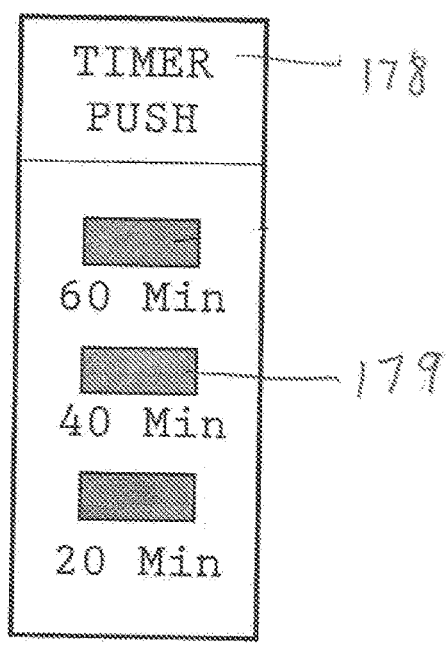

FIG. 14a shows a front view of a granular timer 175. FIG. 14B shows the interior of granular timer 175 when its reservoir 178 is ruptured, the color granules gradually begins to flow down channels 177A, 177B, 177C, 177D at a precise rate of time. When granules fill the clear windows 176, 179, 180, color granular will then be seen indicating the time marked for that window. Dangle or slack holder 12 (FIG. 1) helps keep the timer in a straight up position to allow granules to flow freely. The timer has a sticky tape so it can be placed on tourniquet end. Another way the timer can be made is by having a strip that has absorbent paper between two outside strips a reservoir that holds a colored liquid (Pine oil), the strip also has windows that have time markings similar to the granular timer, the pine oil is held in a reservoir. When the reservoir is ruptured it releases the pine oil and begins to be absorbed by the paper, at precise rate of time, as the color pine oil pass each window that will indicate the elapsed time. The strip has a surface that has glue so it can be placed on and off of the tourniquet. The time strip can be made to automatically rupture the reservoir as time strip passes through elements 3 and 13 of the head which press against time strip reservoir.

The above-described tourniquet embodiments of the present invention produce features and functionalities that are far superior to what has been provided in the tourniquet marketplace to date, including quick application time of 6 seconds or less, resulting in quick blood flow occlusion in the extremities. These tourniquets can also be used on torso wounds to hold pressure dressings in place. The size and versatility of these tourniquets make them suitable for being used with adults, children and animals because of the small circumference after the tourniquet is tightened. First responders can use these tourniquets during terrorist attacks or mass shootings as the time it takes to apply these tourniquets is so short that many injured persons can be treated quickly, saving their lives.

The pressure in these tourniquets can be released by a highly visible one finger release lever, the tension releasing in increments of millimeters to reduce pain and to allow for complete or partial occlusion, while eliminating pinching of the skin. The automatic self-locking mechanism can be applied in total darkness due to audible clicks when applied properly. The material of which the tourniquet is built is bullet resistant and comes packaged pre-loaded and made of memory material which brings into a ready to apply position when removed from the package. It has a non-lip finger hold pull tab that is able to automatically clean itself when applied.

Figure 15:
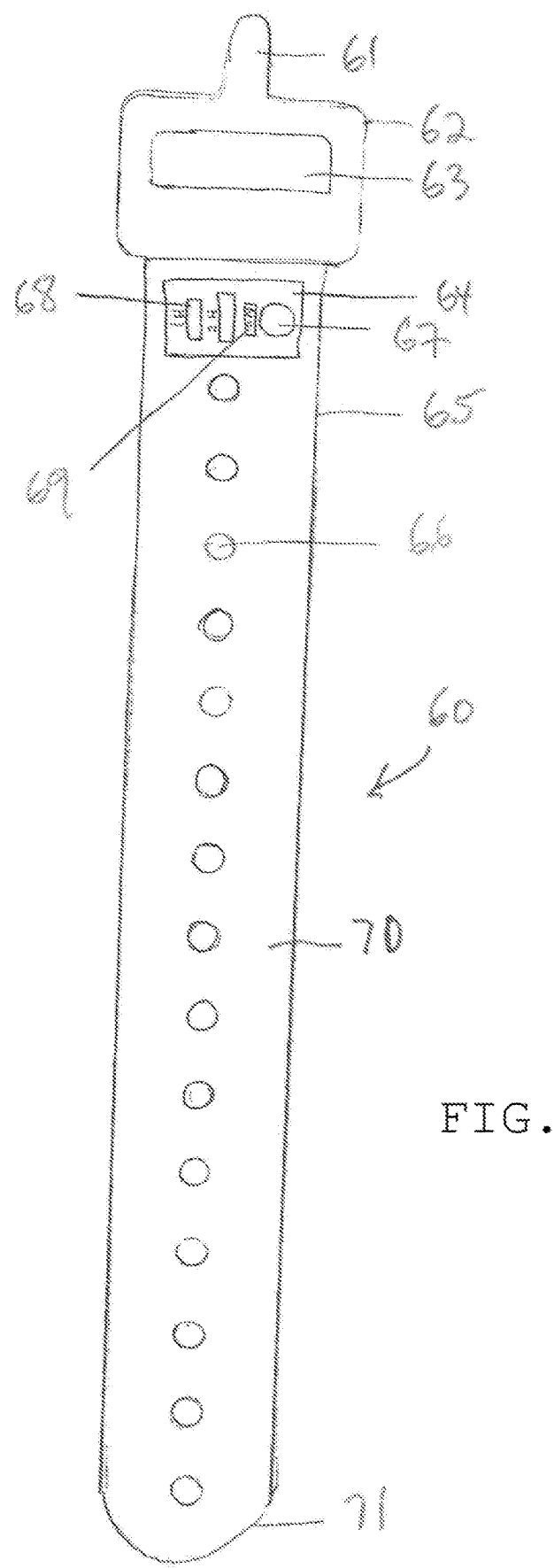
FIG. 15 shows a further embodiment of a tourniquet in accordance with the present invention incorporating a timer.

Referring now to FIG. 15, a more simple but effective tourniquet 70 is illustrated which has a general belt shape with a strap body 70 comprising a series of locking holes 66 which can be engaged by the locking pins 61 of a buckle head 2 which comprises a buckle opening or mouth 63 through which the strap body 70 can be passed.

Of particular interest to this embodiment is the more elaborate timer 64, which comprises an "on indicator" window 67 with timer window 68, for example a one hour window and a two hour window and with an "on indicator" 69.

This embodiment featuring the timer 64 enables the victim or first responder to know how long the tourniquet has been applied. As before, the tourniquet 60 is designed to be placed on extremities of limbs in order to occlude blood flow. In operation, the belt strap 65 is placed around an extremity and the distal end 71 thereof is inserted into the buckle opening 63. The distal end 71 is pulled sufficiently tied until the blood flow is occluded, at which point the locking pin 61 engages any one of the belt holes 66 and, simultaneously, the timer 64 is activated. The timing function is commenced by the user pressing down on the reservoir 67 to rupture the reservoir and begin the flow of liquid, as previously described.

Referring now to FIGS. 16-20, the present invention also incorporates a novel windlass tightening mechanism for the tourniquets of the present invention, providing a means to increase the tension that the straps 6 exert on the limb after it has been donned and tightened. This is in effect a secondary tensioning mechanism to tighten the tourniquet.

Figure 16:
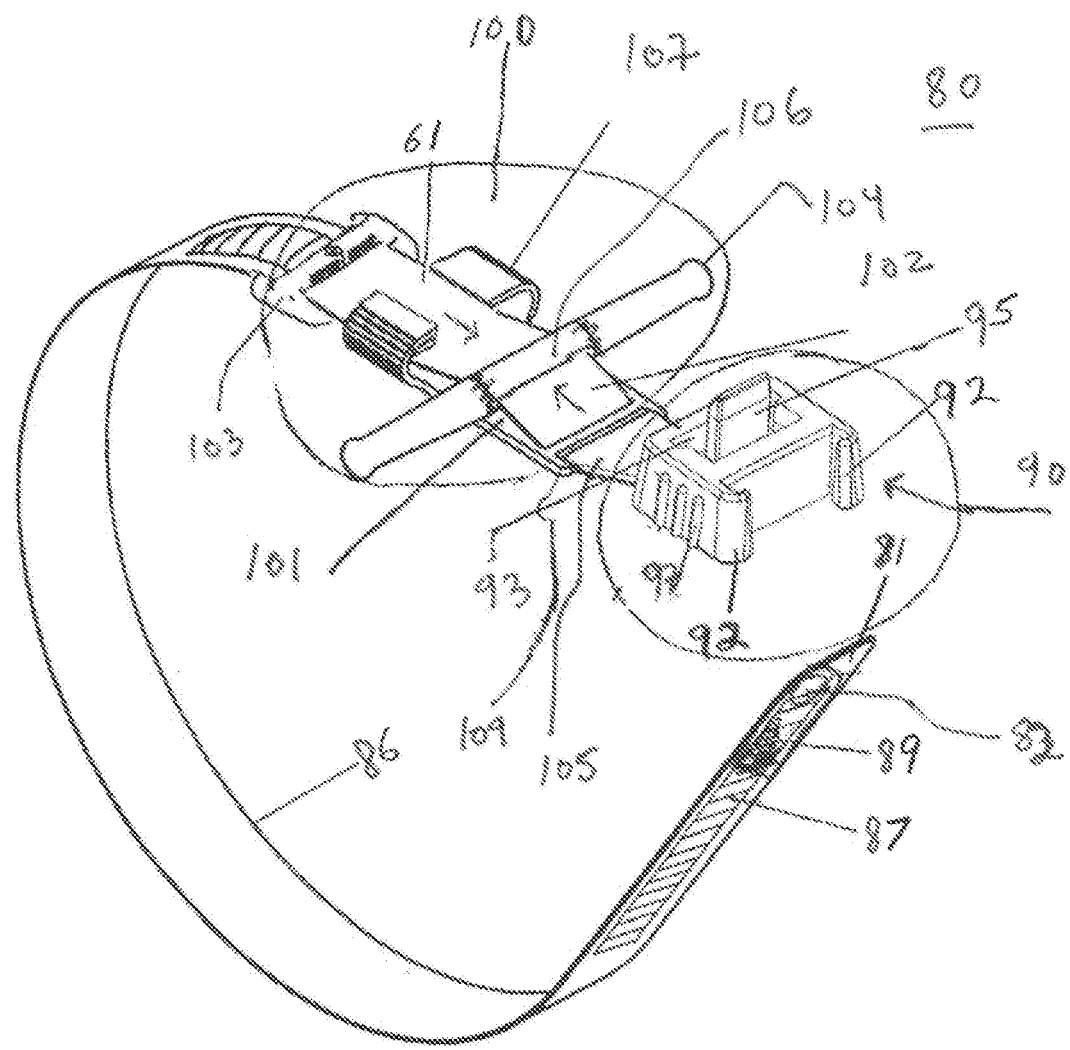
FIG. 16 perspectively illustrates a further tourniquet embodiment with a windless, secondary tension adjusting device.

Referring to FIG. 16, the present tourniquet 80 comprises a head 90 similar to the one previously described with a mouth 93 with ridges (not shown) therein, a tension release lever 95 and with an inwardly extending strap retainers 92. The head 90 comprises holding knurled projections 97.

As described before, the distal end 81 of the strap 86, which has on one side thereof the ridges 87 and the leading edge the timer 89 and the pulling opening 82 is inserted through the mouth 93 as before.

The further improved tourniquet 80 differs in one aspect from the previously described embodiments in that the non-free end is not directly connected to the head 90. Instead, the secondary tensioning mechanism 100 is interposed therebetween and includes first and second buckles 103, 105, with the first buckle being a coupling the strap and the second buckle 105 being connected to the head 90. A base 101 made of substantially soft material and having a pair of clips 107 to hold the tightening rod after it has been used to tension it extends from the soft body 101. A soft strip body 106 is threaded through an opening in the bottom or through the middle 104 and is connected at one end thereof to the rigid body 101 and at a second thereof to the buckle 103. Thereby, when the bar 104 is turned either clockwise or in the opposite direction (see FIG. 20), the soft tightening material 102 naturally shortens, pulling with tremendous force, pulling on the strap thereby applying additional tension to the limb on which the tourniquet 80 has been applied to. Once sufficient pressure has been applied, one of the distal ends of the tightening rod 104 is placed in the clips and locked therein, holding the secondary tension without release.

Figure 17:
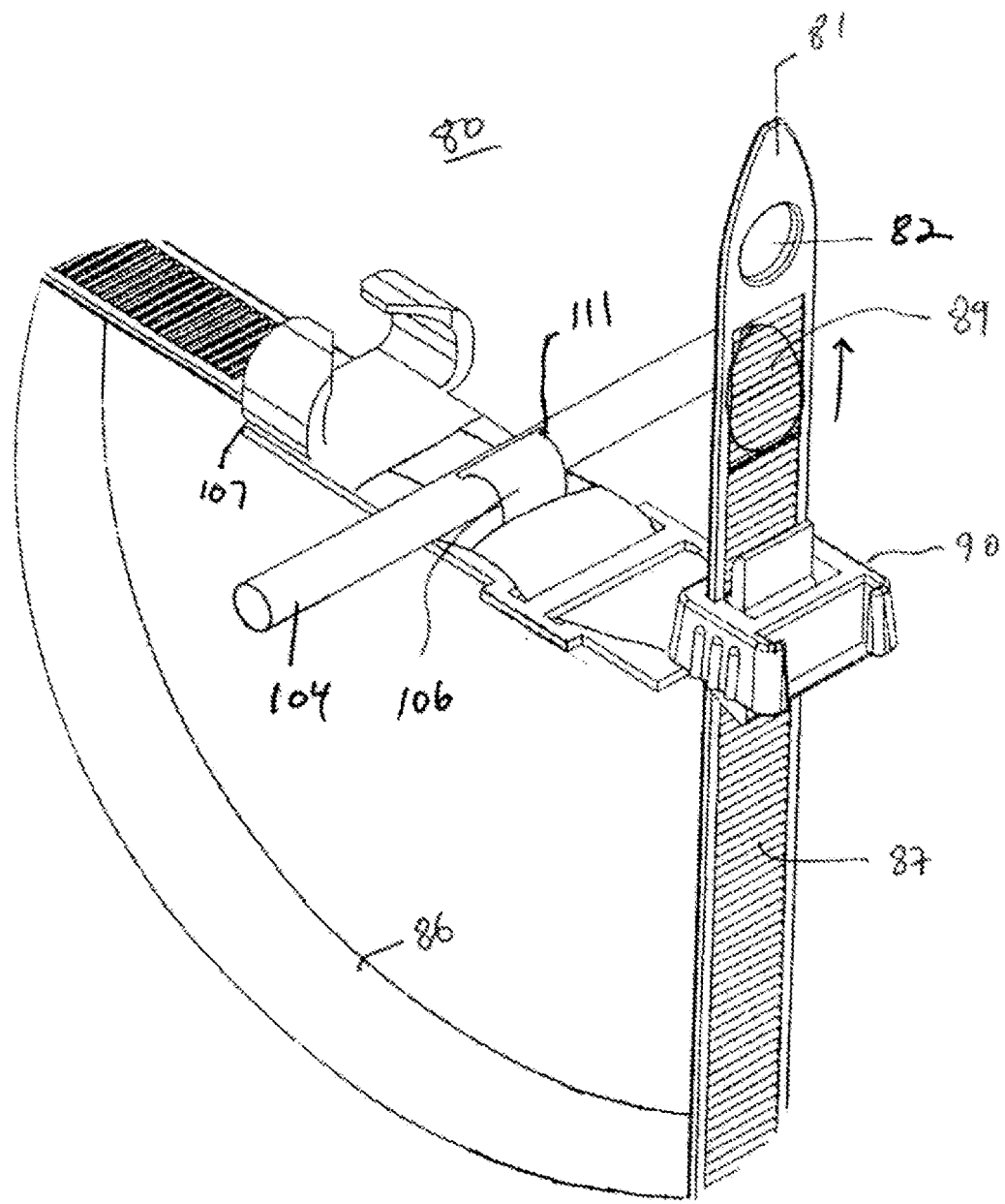
FIGS. 17 and 18 are perspectives that illustrate the tourniquet of FIG. 16, in use.

Further details of the tourniquet 80 can be discerned from FIG. 17 which shows the distal or leading ends 81 having been passed through the heads 90. When the sufficient tension has been attained, the access free end is folded over and passed through the retaining clips 92 as shown in FIG. 18.

Figure 19:
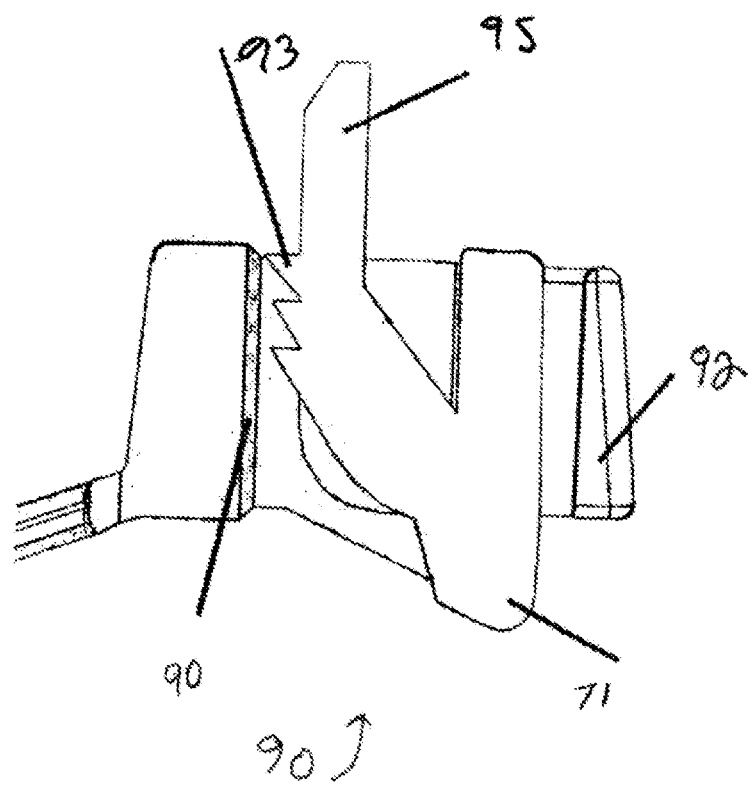
FIG. 19 is a cross section through the head portion of the tourniquet of FIG. 16.

Details of the head itself are very similar to as before and as shown in FIG. 19 comprises the internal teeth 93 and the tension release lever 95.

Figure 20:
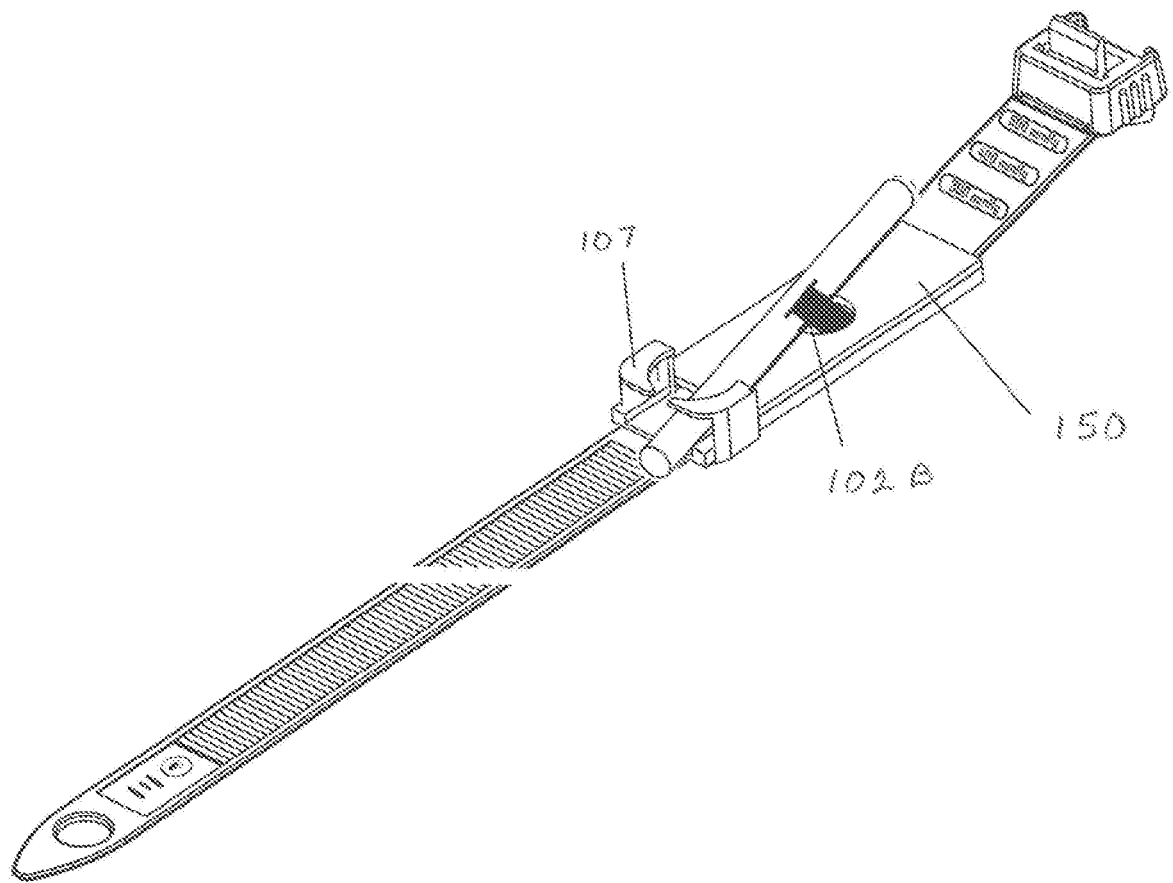
FIG. 20 illustrates the rod locking feature of the tourniquet of FIG. 16.

FIG. 20 also shows that the soft plate 101 may be either integrally formed with the clips 107 or otherwise attached thereto.

Reference is now made to FIG. 21 which shows the windlass tensioning mechanism 90 with a covering sleeve 120 formed over the construction with only a small piece of the soft material 102 protruding through a circular hole 102a. The sleeve can be seen in a side view on FIG. 22.

Figure 23:
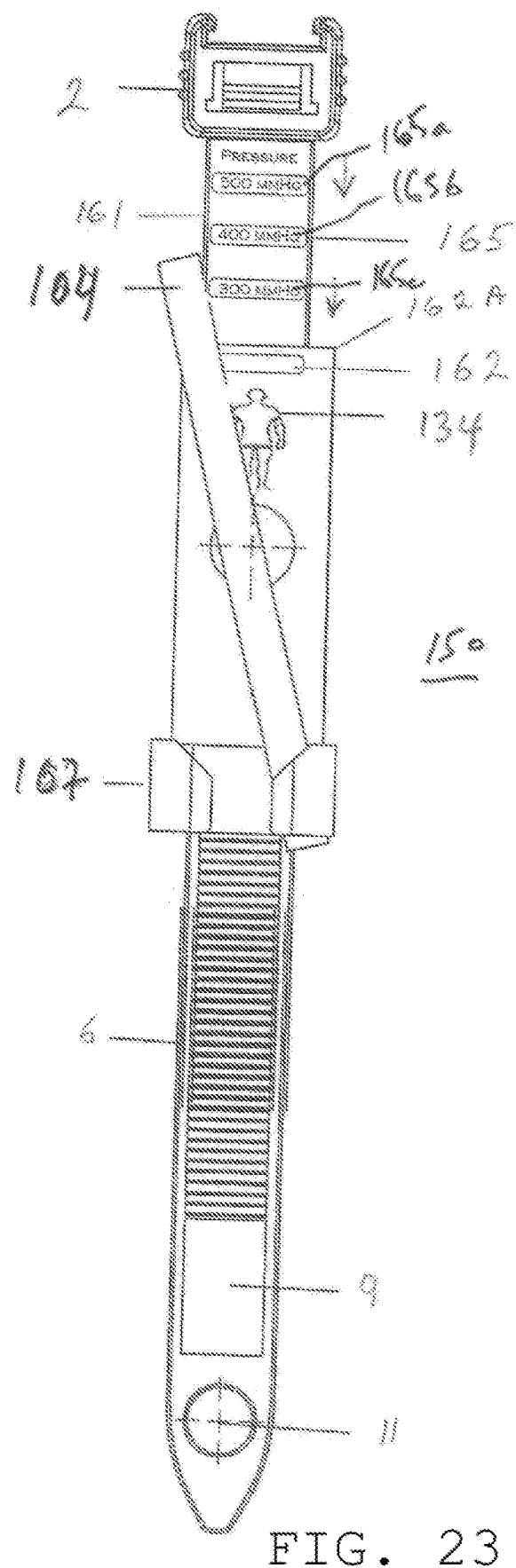
FIG. 23 illustrates the tourniquet of FIG. 21, with a device that displays the pressure being applied to the patient's limb.

Referring to FIG. 23, a front view is provided of a modified tourniquet 150 which has the general construction of the previously described tourniquets, but which also includes at the portion 161 a pressure measuring and displaying assembly 165 that has strips 165a, 165b, 165c that activate when the pressure being applied reaches set, predetermined values, for example, 500 mmHg, 400 mmHg and 300 mmHg, respectively. The pressure readings may be in pounds, millimeters of mercury or any measurement that senses and displays the applied pressure or tension. This information is helpful when teaching how to apply a tourniquet or pressure strap to occlude blood flow, for example, on a child vs. adult; the pressure measuring device and assembly is only activated when auxiliary tension rod is used.

Figure 24:
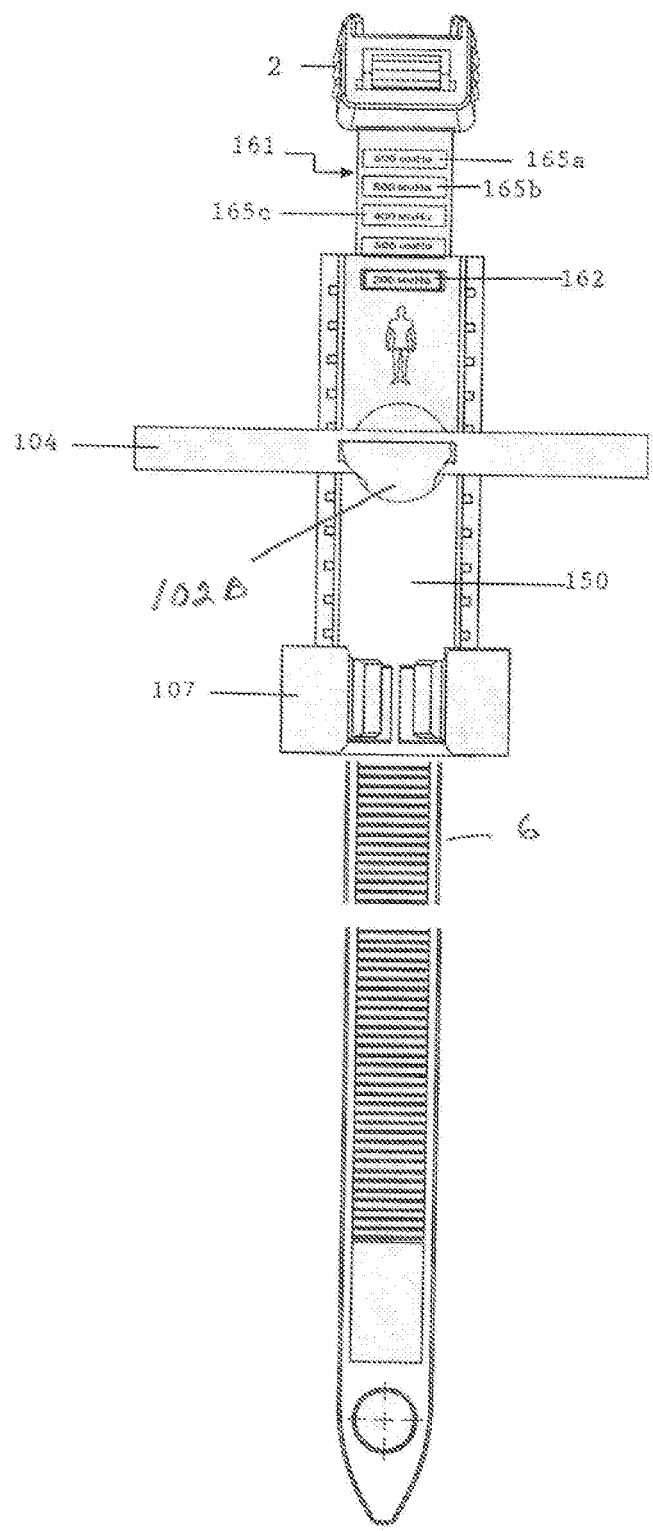
FIG. 24 illustrates a further developed windlass feature associated with a timing device of the present invention.

With reference to FIG. 24, in the tensioning and timing scheme illustrate here, a tourniquet pressure scale 161 is shown. After the tourniquet is applied around the limb, by inserting the strap end 11 into head 2 and pulling the strap end 11 snug around the limb; followed by rotating 104, the tension rod pull in the pressure scale 161 into base 150, thus further tightening the tourniquet around limb as the pressure number (elements 165a and 165b) appear in the indicator window 162. That number indicates the pressure that is being applied. The pressure readings can be in millimeters of mercury or in pounds or any other measurement that indicates tension. The existing tension numbers are pre-determined and gauged by using a known, so-called HapMed digital leg simulator that is used to gauge how much pressure is being applied by a tourniquet to an electronic leg simulator, the amounts of pressure are marked on the tourniquet and used as a template for all other tourniquets. The pressure numbers can also be in different colors to make reading easier. The V shape protrusion at the bottom of the head allows the strap to enter the mouth of head in a straight position to allow ridges on the strap to interlock with the teeth in the head.

Referring to FIGS. 24a through 24d, the windlass tourniquet section of FIG. 24 is shown therein disassembled. The strap section pressure scale 161 and head 2 of FIG. 6 are modified by the including the fabric material 102A that joins strap 6 with pressure scale 161. Fabric material 102A is placed into channel 170B at the bottom half of base 150. A top part 170A of base joins onto element 170C. Section 102B of the fabric is placed inside of hole 102A and tension rod opening 104A. When the tension rod 104 is rotated, section 161 is pulled into channel 170B, thus shortening the circumference length of the tourniquet. It also draws the pressure scale section 161 into the base, causing the pressure gauge numbers to be seen in window 162 of FIG. 24c, which indicates the amount of pressure being applied to a limb. This is especially useful for the "Stop the Bleed" campaign instructors when teaching the 250 million people they intent to teach on how to apply a tourniquet to a victim of a terror attack; it helps to show a student how much pressure is needed for different size and shape individuals.

Figure 26:
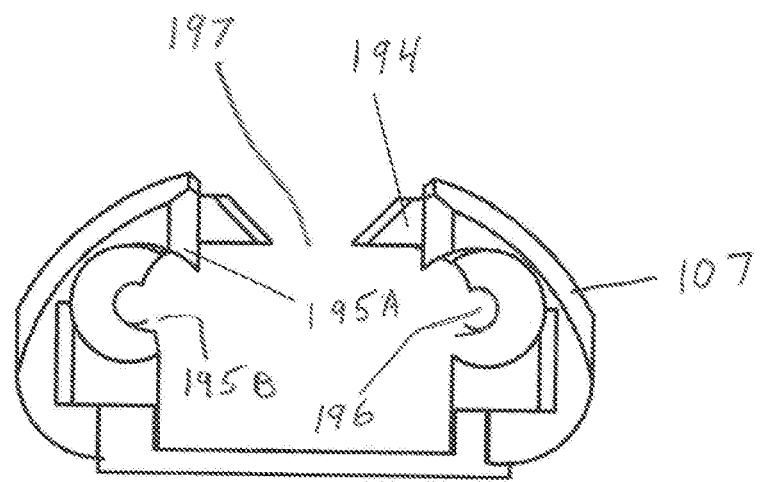
FIGS. 25 and 26 explicate the manner in which the windlass device can be mounted to the strap of the tourniquet of the present invention.
Figure 25:
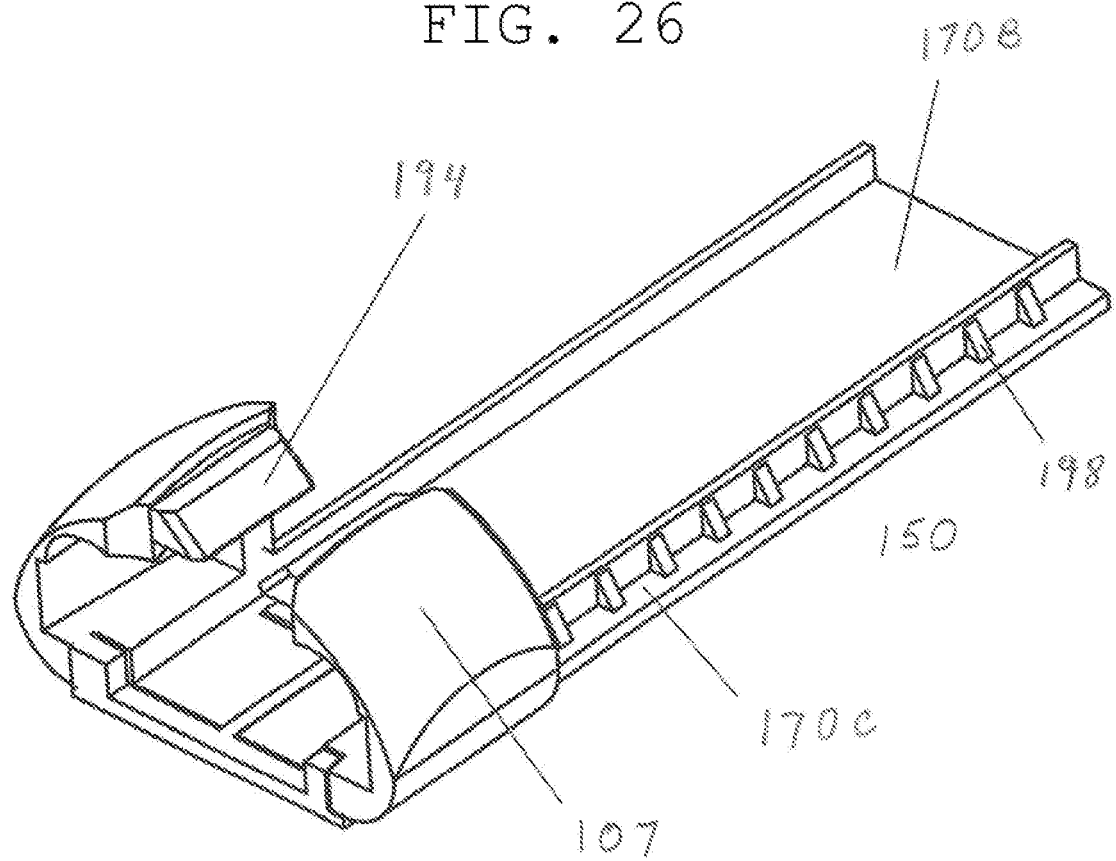

With reference to FIGS. 25 and 26, the clip 107 holds the tension rod 104, preventing accidental rod unwinding. Clip 107 is attached to the windlass base 150. Protruding piece 194 (FIG. 26) is angled to guide and allow the tension rod to be easily guided into a locking position in the nesting notch 196. Protruding piece 195A keeps the rod 104 from becoming released out of opening 197. FIG. 25 shows a top view of base 150, and holding clips 107. Supports wall 198 support base 150.

Figure 27:
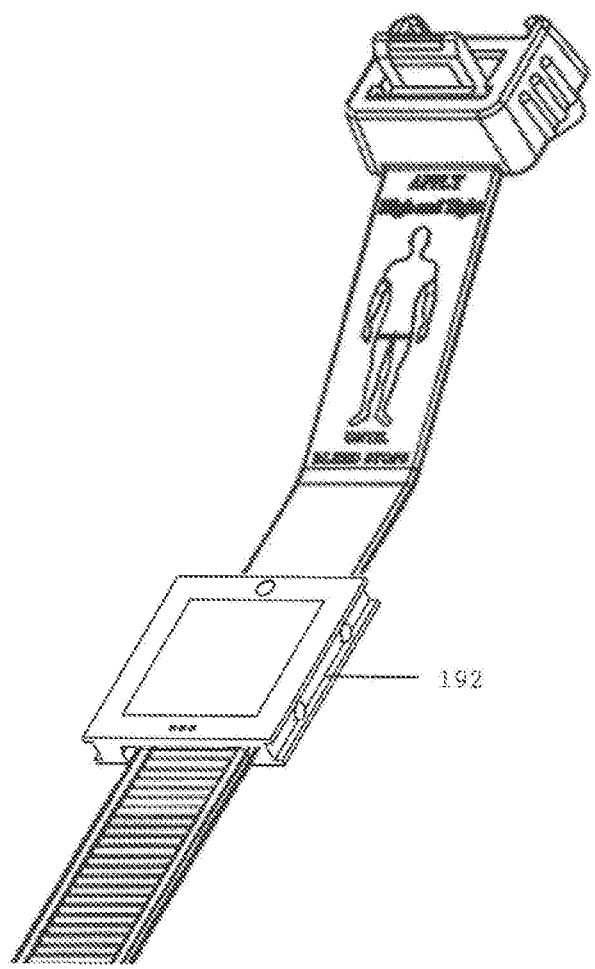
FIG. 27 illustrates a multi-sensor medical testing device that can be mounted to the tourniquets of the present invention.
Figure 29:
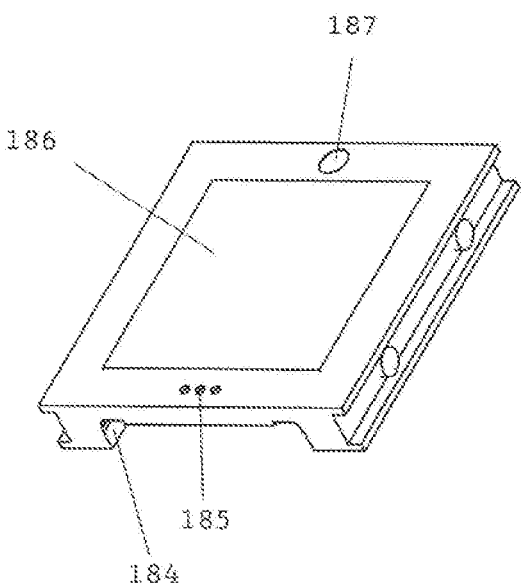
FIGS. 28, 29 and 30 depict details of the medical testing device of FIG. 27.
Figure 30:
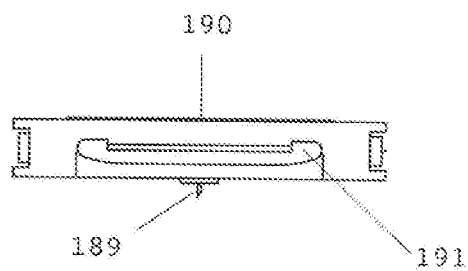
Figure 28:
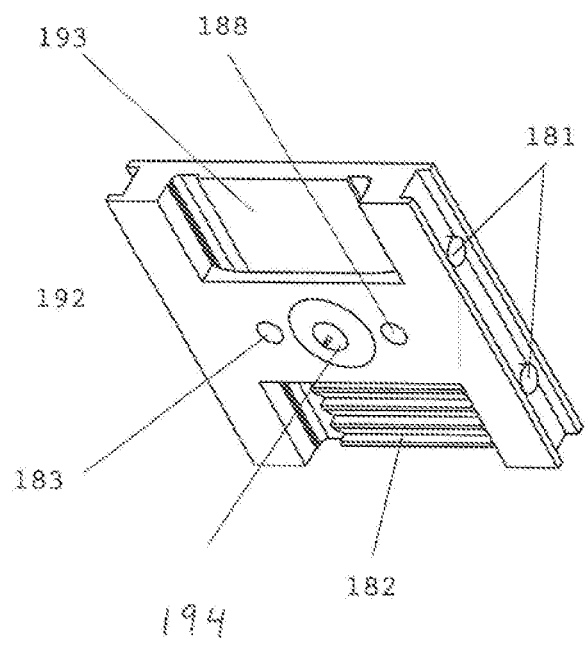

FIG. 27 shows a perspective, top view of a medical sensor 192 that slides onto the tourniquet. FIG. 28 shows bottom and side views of medical sensor 192 that retro fits the tourniquet and touches the skin when the tourniquet is applied. LEDs 183 and 188 read the pulse and oxygen levels in the blood, respectively, and multi-function on/off buttons 181 control operations of the sensor 192. The teeth 182 interlock with the teeth/ridges on the tourniquet strap, shown in prior embodiments. The channel/opening 193 allows the tourniquet strap to slide in, enabling the sensor 194 to read perspiration and temperature. FIG. 29 is a top view of the medical sensor showing the liquid quartz 186 which displays vital sign readings. The speaker 185 alerts a victim of a more than 20% blood loss, which marks the point of going into hypovolemic shock, low body temperature and abnormal body sweats. The protruding sides 184 enable the tourniquet to slide into and help hold and guide the tourniquet. LED 187 indicates another function. FIG. 30 shows an end view of the medical sensor and shows a protruding needle 189. By pressing down on top of medical sensor 190 the needle pricks the skin to also check blood sugar levels which can drop drastically when bleeding, and cause a patient to go into shock. An example of a similar medical sensor can be observed at www.giantbiosensor.com.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A tourniquet, comprising:
a strap formed of a flexible material and being shaped as a long and generally flat body having a first surface and an opposed second surface, and an array of ridges extending transversely, substantially along most of the first surface;
a tourniquet head including an insertion mouth and within the mouth there being provided a flexible support and a plurality of teeth formed on the flexible support, said flexible support and said plurality of teeth providing an insertion channel in the tourniquet head for tightly receiving a free insertion end of the strap in a manner that enables the strap to be threaded through the insertion mouth with the plurality of teeth in the head being lockable on the ridges on the strap in a manner that enables a leading end of said strap to be ratcheted through the mouth in a locking direction only; and
a release lever that enables said flexible support in the mouth to be pulled away from the ridges on the strap to allow for temporary disengaging of the teeth in the head from the ridges on the strap, to enable gradual and controlled releasing of tourniquet tension being applied on a body part to which the tourniquet has been mounted, further comprising an auxiliary tourniquet tensioning device comprising a tensioning rod that can be twisted to shorten the length of the strap to increase a tension being applied to the human body part.

2. The tourniquet of claim 1, further including at least one holding device configured to be coupled to the strap, at a desired location on the strap, said holding device being configured to be placed on an injury location on the human body part, the holding device holding one or more of; a pressure sensing device, medicinal material, a temperature sensor, a light emitter, a sound emitter, a GPS location sensor, a pulse sensor, an oxygen level blood saturation sensor, a gauze coated with blood coagulant, a perspiration sensor and an LCD screen.

3. The tourniquet of claim 2, wherein said GPS location sensor comprises a wireless device that transmits GPS coordinates of the tourniquet.

4. The tourniquet of claim 2, wherein the perspiration sensor is configured to determine if a patient has entered into hypovolemic, hemorrhagic shock or other medical conditions from loss of blood.

5. The tourniquet of claim 2, including a needle that protrudes on the bottom of a medical sensor, so that when medical sensor is pressed down onto skin the needle penetrates the skin in order to provide more accurate medical testing of blood and skin.

6. The tourniquet of claim 1, wherein said tourniquet is configured to increase the pressure on the human body part by holding the head thereof in one hand and pulling on a tail end of a strap with another hand and further including a separate ratcheting lever that is configured to enable further tightening of the strap, to increase the tension exerted by the tourniquet by ratcheting the ratcheting lever to engage the ridges on the strap, one ridge at a time.

7. The tourniquet of claim 1, wherein the head comprises an insert holding clip for holding a dangling portion of the strap down over the release lever on head, to prevent undesired releasing of tourniquet pressure being applied to the human body part.

8. The tourniquet of claim 1, wherein the head of the tourniquet is configured to allow at least two of the tourniquets to be interconnected, allowing binding of extremities together or supporting a fractured hip or a fractured skull, or to be used on a torso as a pressure strap.

9. The tourniquet of claim 1, wherein the strap has, adjacent its insertion end, a pulling opening through which a finger can be inserted to tightly grasp the strap when being pulled, without slipping.

10. The tourniquet of claim 1, further including a timer that is initiated at the time when the tourniquet is applied around the human body part.

11. The tourniquet of the claim 10, wherein the timer comprises a reservoir of colored liquid, so configured that when the reservoir is ruptured, the color liquid flows at a precise rate along a channel that leads to a number of windows, each window indicating a different elapsed time.

12. The tourniquet of claim 11 timer, including alcohol in the reservoir.

13. The tourniquet of claim 11, wherein the liquid comprises pine oil.

14. The tourniquet of claim 10, further including a granular timer using color granular particles to eliminate liquid evaporation.

15. The tourniquet of claim 10, wherein the timer is removeably attachable to the strap adjacent its insertion end, so it is capable of being activated either manually or automatically when the strap is inserted into the insertion mouth of the head.

16. The tourniquet of claim 10, wherein the timer comprises a digital timer.

17. The tourniquet of claim 1, further including visually perceptible instructions for mounting the tourniquet to a human patient, wherein the visual instructions comprises a silhouette of a human body illustrating locations where the tourniquet should be applied.

18. The tourniquet of claim 1, including a holding device configured to hold a location indicator that emits one of visible light and infrared radiation, to allow visible location of a victim bearing the tourniquet.

19. The tourniquet of claim 1, wherein the tourniquet is provided in a package with its insertion end already threaded through the insertion mouth at the head, so it is ready to be deployed during emergencies without loss of time by simply being placed around a human limb and then tightened.

20. The tourniquet of claim 1, wherein the auxiliary tensioning mechanism comprises a windlass locking mechanism.

21. The tourniquet of claim 20, wherein the windlass locking mechanism comprises a pair of plates, including a top plate and a bottom base plate, interposed between the head and the strap, the plates being attached together by a flexible fabric material.

22. The tourniquet of claim 21, further comprising a further fabric material and the further fabric material contacting the tensioning rod in a manner so that when the tensioning rod is twisted, the fabric material shortens a circumferential dimension of the tourniquet about the human body part.

23. The tourniquet of claim 20, further comprising a clip mechanism configured to prevent the tensioning rod from untwisting.

24. The tourniquet of claim 1, wherein the ridges are spaced at a separation in the range of 1 to 3 millimeters, to allow fine adjustment of the tension being applied to the human body part.

25. The tourniquet of claim 1, wherein the strap is formed of a mixture of thermoplastic polyurethane (TPU) material that is bullet, oil, water and dirt resistant, and self-sealing when punctured.

26. The tourniquet of claim 1, wherein the strap ridges extend from a distal end of the strap to the head, enabling the tourniquet circumference to be tightened down to a few millimeters so it can be used on children, adults and animals.

27. The tourniquet of claim 1, wherein pulling the insertion end of the strap through the head produces audible sounds as each ridge on the strap is passed through the head, to provide an audible indication of a properly applied and functioning tourniquet.

28. The tourniquet of claim 1, wherein said plastic material of said strap is capable of withstanding temperatures of −55° to 155° Fahrenheit, without losing its functionality.

29. The tourniquet of claim 1, further including a section of the strap that is coated with paint that allows for scrapping with a pointy object or fingernail the time the tourniquet was applied and other information.

30. The tourniquet of claim 1, including a section of the tourniquet having a strip that can be applied to and removed from the tourniquet, allowing writing a time the tourniquet was applied and other information.

31. A tourniquet, comprising:
a strap formed of a flexible material and being shaped as a long and generally flat body having a first surface and an opposed second surface, and an array of ridges extending transversely, substantially along most of the first surface;
a tourniquet head including an insertion mouth and within the mouth there being provided a flexible support and a plurality of teeth formed on the flexible support, said flexible support and said plurality of teeth providing an insertion channel in the tourniquet head for tightly receiving a free insertion end of the strap in a manner that enables the strap to be threaded through the insertion mouth with the plurality of teeth in the head being lockable on the ridges on the strap in a manner that enables a leading end of said strap to be ratcheted through the mouth in a locking direction only; and a release lever that enables said flexible support in the mouth to be pulled away from the ridges on the strap to allow for temporary disengaging of the teeth in the head from the ridges on the strap, to enable gradual and controlled releasing of tourniquet tension being applied on a body part to which the tourniquet has been mounted, wherein the head has a separate lever located at a back wall of the head that is configured to apply further tensioning of the strap, to increase the tension exerted by the tourniquet.

32. A tourniquet, comprising:

a strap formed of a flexible material and being shaped as a long and generally flat body having a first surface and an opposed second surface, and an array of ridges extending transversely, substantially along most of the first surface;

a tourniquet head including an insertion mouth and within the mouth there being provided a flexible support and a plurality of teeth formed on the flexible support, said flexible support and said plurality of teeth providing an insertion channel in the tourniquet head for tightly receiving a free insertion end of the strap in a manner that enables the strap to be threaded through the insertion mouth with the plurality of teeth in the head being lockable on the ridges on the strap in a manner that enables a leading end of said strap to be ratcheted through the mouth in a locking direction only;

a release lever that enables said flexible support in the mouth to be pulled away from the ridges on the strap to allow for temporary disengaging of the teeth in the head from the ridges on the strap, to enable gradual and controlled releasing of tourniquet tension being applied on a body part to which the tourniquet has been mounted; and a pressure indicating device that senses the pressure that is applied to the strap of the tourniquet to the human body part in units of pressure which is indicated in one of a reading provided in pounds or millimeters of mercury (mmHg) or in color scale.

* * * * *